US005653991A

United States Patent [19]

Rod

[11] Patent Number: 5,653,991
[45] Date of Patent: Aug. 5, 1997

[54] PROCESS FOR REPELLING AND KILLING INSECTS AND COMPOSITIONS TO EFFECT THE SAME COMPRISING A MONOTERPENE

[75] Inventor: Robert L. Rod, Marina del Rey, Calif.

[73] Assignee: The Rod Family Trust, Marina Del Ray, Calif.

[21] Appl. No.: 437,539

[22] Filed: May 9, 1995

Related U.S. Application Data

[63] Continuation-in-part of Ser. No. 36,363, Mar. 24, 1993, abandoned.

[51] Int. Cl.⁶ ..................................................... A01N 25/32
[52] U.S. Cl. ........................ 424/406; 424/405; 514/762; 514/763; 514/764; 514/765; 514/766; 514/703
[58] Field of Search .................................. 424/405, 43, 47, 424/70.1, 70.12, 70.121, 78.02; 514/63, 473, 762–766, 703

[56] References Cited

U.S. PATENT DOCUMENTS

| | | | |
|---|---|---|---|
| 1,949,799 | 3/1934 | Knight | 514/762 |
| 2,988,473 | 6/1961 | Mallis et al. | 514/762 |
| 3,033,144 | 2/1962 | Greathouse | 167/58 |
| 3,227,609 | 1/1966 | Wilson et al. | 514/762 |
| 4,379,168 | 4/1983 | Dotolo | 424/356 |
| 5,045,536 | 9/1991 | Baker | 514/63 |
| 5,143,900 | 9/1992 | Steltenkamp et al. | 512/26 |
| 5,372,806 | 12/1994 | Holloway | 424/70.1 |
| 5,393,791 | 2/1995 | Roberts | 514/762 |

*Primary Examiner*—Neil S. Levy
*Attorney, Agent, or Firm*—Sherman and Shalloway

[57] ABSTRACT

Closely related formulations of GRAS food additives serve as insect repellents, insecticides and larvicides. The ingredients of the repellent, insecticide and larvicide also exhibit useful disinfectant properties against vector-borne pathogenic microorganisms.

4 Claims, No Drawings

1

PROCESS FOR REPELLING AND KILLING INSECTS AND COMPOSITIONS TO EFFECT THE SAME COMPRISING A MONOTERPENE

CROSS-REFERENCE TO RELATED APPLICATIONS

This application is a continuation-in-part of application Ser. No. 08/036,363, filed Mar. 24, 1993 now abandoned.

BACKGROUND OF THE INVENTION

1. Field of the Invention

The present invention relates to the field of insect repellents and insecticides. More particularly, the present invention is directed to processes for repelling and killing insects, compositions for repelling insects, compositions for killing insects, and the preferred use of a monoterpene, as well as other generally regarded as safe (GRAS) food additive materials, for the formulation of such compositions.

2. Description of the Prior Art

The control of insects, both for the protection of crops and animals, and for the maintenance of public health, has consumed much study and effort over the years. Ten percent of the food man produces is eaten by insects. Consequently, the control of insects to protect crops and livestock is of paramount importance, especially for farmers.

Insects are also especially commonplace in and around homes. Insects, such as flies, mosquitos, cockroaches and fleas ordinarily may function as vectors for contagious diseases.

Three main methods of chemically controlling insect pests are known and used; namely stomach poisons, contact poisons and fumigants. In the past, when there was less concern about the environment, little attention was paid to the toxicity of organic and inorganic materials employed to control insects. Today, virtually all the insect repellents and insecticides presently registered with the U.S. Environmental Protection Agency bear warnings prohibiting their use near food or in food-serving places and in waters bearing fish. Many of these insect control agents are toxic to humans if ingested, inhaled or physically contacted. There is a thus a demand for safer pesticides equal in efficacy to the more toxic ones presently available.

One area of interest in the production of environmentally safe insect repellents and insecticides is the use of Generally Regarded As Safe (GRAS) food flavorings. The monoterpene known as d-limonene is approved for use as a GRAS essential oil, food flavoring additive in foods eaten by humans (21 CFR, part 170–199, Food and Drugs, dated Apr. 1, 1990, incorporated herein by reference) and is similarly listed in the internationally recognized FOOD CHEMICALS CODEX (3d ed.) (incorporated herein by reference). This comparatively fast evaporating essential oil is derived from the peels of citrus fruit. Its fragrance has long been known to be a strong natural insect repellent and insecticide. In nature, for example, termites spray a naturally manufactured terpene at attacking ants to keep them at bay. Various terpenes, including d-limonene, are found in bark, and both repel and kill insects which attack living trees.

The natural repellency and insecticidal properties of d-limonene and its chemically related terpenes have been well documented for many years in scientific journals. More recently, in 1983, Dotolo, in U.S. Pat. No. 4,379,168, taught the limited use of d-limonene only as an insecticide and not as a repellent when mixed with surfactants, water, and a required antioxidant to keep the d-limonene from going rancid in the presence of air. However, the use of large volumes of water as specified in Dotolo's patent dilutes the efficacy of d-limonene.

The ability to repel animals, in general, and insects, in particular, may also be achieved by GRAS flavorings. U.S. Pat. No. 3,923,997 teaches the use of α-n-alkyl-γ-butyrolactone and/or a δ-valerolactone as an anti-mating composition or as a repellent for animals.

SUMMARY OF THE INVENTION

It is an object of the present invention to provide a process for killing insects having a protective wax waterproofing coating covering their bodies to prevent desiccation. The process comprises wetting the insect with an effective amount of a solution of a terpene of the formula $C_{10}H_{16}$ and a fast evaporating white mineral oil to destroy the wax waterproofing coating, the fast evaporating white mineral oil having a distillation initial boiling point of between 350° F. and 410° F., an end point of from 405° F. to 516° F. and a flash point of about 142° F. to 165° F. The solution utilized in the process may further con-tain one or more of an aldehyde, a silicone fluid and a surfactant.

It is a further object of the present invention to provide a process for repelling insects attracted to a locus by an odor emitted from the locus. The process comprises wetting the locus with an effective amount of a solution of a terpene of the formula $C_{10}H_{16}$ and a slow evaporating white mineral oil to mask the odor emitted from the locus, the slow evaporating white mineral oil having a distillation initial boiling point of at least 360° F., an end point of 600° F. and above and a flash point of from 245° F. to 590° F. The solution utilized in the process may further contain one or more of an aldehyde and a fragrance.

It is a yet further object of the present invention to provide a process for repelling mosquitoes from mammals (i.e., animals or human) comprising wetting the exposed skin surface of an animal or a human with an effective amount of a solution of a terpene of the formula $C_{10}H_{16}$ and a slow evaporating white mineral oil, the slow evaporating white mineral oil having a distillation initial boiling point of at least 360° F., an end point of 600° F. and above and a flash point of from 245° F. to 590° F.

It is a still further object of the present invention to provide a process for killing mosquito larvae comprising spraying a solution of a terpene of the formula $C_{10}H_{16}$ and a white mineral oil base onto the surface of waters in which mosquitoes breed, the white mineral oil base comprising a mixture of a fast evaporating white mineral oil and a slow evaporating white mineral oil in a weight ratio of 1:99 to 99:1, respectively; the fast evaporating white mineral oil having a distillation initial boiling point of between 350° F. and 410° F., an end point of from 405° F. to 516° F. and a flash point of about 142° F. to 165° F.; the slow evaporating white mineral oil having a distillation initial boiling point of at least 360° F., an end point of 600° F. and above and a flash point of from 245° F. to 590° F.

It is a yet further object of the present invention to provide a process for killing and repelling whitefly comprising wetting all plant leaf surfaces at the locus of whitefly infestation with a solution of a terpene of the formula $C_{10}H_{16}$ and a white mineral oil base, the white mineral oil base comprising a mixture of a fast evaporating white mineral oil and a slow evaporating white mineral oil in ratios of 1:99 to 99:1, respectively; the fast evaporating white mineral oil having a distillation initial boiling point of between 350° F. and 410° F., an end point of from 405° F. to 516° F. and a flash point of about 142° F. to 165° F.; the slow evaporating white mineral oil having a distillation initial boiling point of at least 360° F., an end point of 600° F. and above and a flash point of from 245° F. to 590° F.

It is a still further object of the present invention to provide a composition comprising a solution of a terpene of the formula $C_{10}H_{16}$ and a white mineral oil base, the white mineral oil base being selected from the group consisting of (1) a fast evaporating white mineral oil having a distillation initial boiling point of between 350° F. and 410° F., an end point of from 405° F. to 516° F. and a flash point of about 142° F. to 165° F., (2) a slow evaporating white mineral oil having a distillation initial boiling point of at least 360° F., an end point of 600° F. and above and a flash point of from 245° F. to 590° F., and (3) a mixture thereof in a ratio of 1:99 to 99:1, respectively. The composition may further contain one or more of an aldehyde, a silicone fluid, a surfactant and a fragrance. Preferably, all components of the composition are components generally rated as safe (GRAS) for use in foods for human consumption, so that the compositions are safe for humans to inhale, ingest or apply to the skin.

DETAILED DESCRIPTION OF THE PREFERRED EMBODIMENTS

The compositions of the present invention include a terpene of the formula $C_{10}H_{16}$ and a white mineral oil base. The compositions may optionally further include at least one aldehyde, at least one silicone fluid, at least one surfactant, and a fragrance.

Terpenes are a class of organic compounds having a common structural feature, i.e., a carbon skeleton of repeating isopentane units $(-CH_2-CH_2-CH(CH_3)-CH_2-)_n$. They are found widely distributed in nature and the lower members of the series, the monoterpenes (n=2) and the sesquiterpenes (n=3) are the major components of the volatile or "essential" oils of most plants. Common terpenes include pine oil derived from wood, alpha-pinene from turpentine and d-limonene extracted from the peel of citrus fruits. In the present invention, it has been found that pine oil, d-limonene, and mixtures of these and other terpenes, such as TABS D (made by Union Camp Corporation), can be used interchangeably or in combination to repel and/or kill insects. However, the pleasant citrus odor of d-limonene, the fact that it is approved as a "generally regarded as safe" (GRAS) food additive by the United States Food and Drug Administration (21 CFR 172.515) and given preference in the Food Chemicals Codex, makes the use of d-limonene a preferred embodiment of the invention. D-limonene is identified as follows:

d-limonene, $C_{10}H_{16}$ p-mentha-1,8-diene, Cinene CAS No. 5989-27-5

The terpene of the formula $C_{10}H_{16}$ is utilized in an amount of 0.1 to 50% by weight based on the total weight of the composition.

The other essential ingredient of the presently contemplated compositions is a white mineral oil base. The nature of the use of the inventive composition will determine the preferred white mineral oil base materials.

Typically, the white mineral oil base is predominantly saturated hydrocarbons with branched, straight chain and/or saturated cyclic structures. The aromatic content is very low and olefins are almost non-existent.

Broadly, the present invention utilizes white mineral oil materials having the following representative properties:

| | |
|---|---|
| API Gravity, 60° F. | 46/50–28/31 |
| Specific Gravity, 60/60° F. | 0.790–0.881 |
| Distillation (ASTM D 86) | |
| Initial Boiling Point (°F., min.) | 350–410 |
| End Point (°F., max.) | 405–600+ |
| Flash Point (ASTM D 92), °F. | 142–590 |
| Carbon Number | $C_{10}$–$C_{18+}$ |

As a practical matter, any widely sold household insecticide generally must evaporate quickly in use without leaving behind stains on floor, carpets, furniture, etc. Heretofore, such hazardous solvents as 1,1,1-trichloroethane, petroleum distillates and fluorocarbons were employed as non-staining propellants in various insecticides used around the home and garden. Environmental considerations regarding the earth's depleting ozone layer have increasingly limited their use today.

The present invention uses no such base materials and employs instead a fast evaporating white mineral oil base, preferably having an average carbon number equal to or greater than 12. (Volatile organic compounds (VOCs) having a carbon number of 12 or higher are exempt from air pollutant controls in California.)

For purposes of this invention, a fast evaporating white mineral oil base is characterized by an initial distillation boiling point of between 350° F. and 410° F., an end point of from 405° F. to 516° F. and a flash point of about 142° F. to 165° F. Suitable oils, which have been approved for use in foods, and elsewhere, are registered under CAS Nos. 64742-14-9 and 64742-47-8 and are available from PENRECO (a division of PENNZOIL PRODUCTS COMPANY).

By choosing a very quick evaporating food-grade white mineral oil solvent as the base and applying the formulation as a contact spray engulfing an insect, the solution of d-limonene and the oil functions as an efficacious household and institutional insecticide.

D-limonene has well-known properties as a household cleaning agent and for use in softening waxes and emulsifying oils that are made use of in the invention. In the insecticide, the solvency properties of the fast evaporating white mineral oil base and the d-limonene together act to destroy the protective wax waterproofing coating covering an insect's body, which leads to its rapid death through desiccation. "Knockdown" is enhanced at the same time by clogging an insect's tiny breathing tubes, called spiracles, with the various oils employed, thus causing suffocation.

The use of mineral oils in the invention has an advantage in that insects do not appear to build up resistance to the lethal suffocating action of an oil-based insecticide as they do against most conventional pesticides. The authoritative referenced publication, *Managing Insects & Mites with Spray Oils* (incorporated herein by reference), states that "Little or no resistance to oils by target pests has been observed."

By combining the terpene of the formula $C_{10}H_{16}$ with a slow evaporating white mineral oil base, a combined insect repellent and skin moisturizer is obtained. Applied to humans and animals, its fragrance deters mosquitoes from landing, probing and then biting. Similarly, its fragrance will also mask those scents which normally attract other insect pests.

For purposes of this invention, a slow evaporating white mineral oil base is characterized by an initial distillation boiling point of at least 360° F., an end point of 600° F. and above and a flash point of from 245° F. to 590° F. Suitable oils, which have been approved for use in foods and elsewhere are registered under CAS No. 8043-47-5, and are available from PENRECO (a division of PENNZOIL PRODUCTS COMPANY).

For purposes of this invention, it is apparent that "effective amounts" will be dependent upon conditions of use. Accordingly, the "effective amounts" will be readily ascertainable by the person skilled in the art through routine experimentation.

Efficacy of the insecticide and the insect repellent can be improved and extended in time by adding small amounts of at least one and preferably two GRAS food-grade slow evaporating essential oil aldehydes. The aldehydes mask those animal body and food odors that attract insects after d-limonene's more volatile fragrance has evaporated. Pungent aldehyde odors also are known mucous membrane irritants to creatures with acute senses of smell, thereby increasing the repellent effect of the invention.

It is preferred that more than one, and more preferably two food-grade aldehydes be used together. The two most preferred aldehydes are:

Gamma-undecalactone, $C_{11}H_{20}O_2$ Aldehyde C-14 pure (so-called), Peach aldehyde Dihydro-5-heptyl-2(3H)-furanone CAS No. 104-67-6

Gamma-nonalactone, $C_9H_{16}O_2$ Aldehyde C-18 Dihydro-5-pentyl-2(3H)-furanone CAS No. 104-61-0

These two aldehydes, like others approved as food flavors, are also commonly identified as lactones. They have characteristic odors of peach and coconut, respectively.

The aldehydes may each comprise from about 0.010 to 5.00% by weight of the total composition.

In a related embodiment, the mixing of fast and slow-evaporating white mineral oils, at ratios of 1:99 to 99:1, by weight, produces an effective and safe mosquito larvicide. This formulation, i.e., the mixed mineral oils, the d-limonene, and any optional ingredients, is sprayed on the surface of waters in which mosquitoes breed. In field tests, conducted by the Entomology Department of The University of California-Riverside, the larvicide has demonstrated 100% efficacy for up to 12 days, suffocating larva coming to the surface to breathe. The all-GRAS formulation of the larvicide appears relatively benign to surface-frequenting organisms that share the habitat and the environment.

The larvicidal formulation has also shown effectiveness combatting the economically disastrous whitefly invasion of food crops in the Southwest region of the United States, in field tests by the University of California's Cooperative Extension at Holtville, Calif. The whitefly is a leaf sucker that desiccates virtually all growing food crops. The formulation is sprayed on all plant leaf surfaces as a combined insecticide and repellent to kill adult insects and their eggs and larva upon contact. The thin oil coating of the invention on leaf surfaces repels other whiteflies from landing by masking plant odors attracting them to their food sources. Test results on row crops and on growing table grapes show the food-grade invention is equivalent to the efficacy of highly toxic insecticides, without phytotoxicity.

It should be noted that d-limonene, in common with the well-known activity of its related terpene, pine oil, and each of the two aldehydes, gamma nonalactone and gamma undecalactone, all display bacteriostatic or bactericidal properties against gram negative and gram positive pathogenic microorganisms. In the concentrations employed in the household insecticide of the invention, the terpene and the two aldehydes showed even stronger activity against four different microorganisms during medical laboratory tests. This is to be expected, as the cell walls of certain microorganisms and some classes of viruses are generally comprised of wax-like lipid materials that often can be broken down by solvents and strong solutions of soap and water. The demonstrated ability of these active materials to break down and thus kill certain insect-borne microorganisms, and eliminate obnoxious odors they cause, has a considerable public health implication as well as economic value, especially in combatting disease-carrying cockroaches and flies in food service locations.

There are other additives that can be used in the invention, either to increase efficacy or to increase the ease with which the products are used.

Repellency against insects can be enhanced by adding one or more of the following food-grade fragrances in amounts of up to about 2% by weight of the composition. They also render the invention more pleasant smelling to human users and are classified as food grade in 21 CFR §172.515:

| | |
|---|---|
| Anethole | Benzaldehyde |
| $C_{10}H_{12}O$ | $C_7H_6O$ |
| CAS No. 104-46-1 | CAS No. 100-52-7 |
| Benzoic Acid | Cinnamyl Alcohol |
| $C_9H_{10}O_2$ | $C_9H_{10}O$ |
| CAS No. 93-89-0 | CAS No. 104-51-1 |
| Musk Ambrette | Oil of Pennyroyal (mixture) |
| $C_{12}H_{16}N_2O_5$ | CAS No. 8007-44-1 |
| CAS No. 83-66-9 | |
| Vanillin | |
| $C_8H_8O_3$ | |
| CAS No. 121-33-5 | |

Additionally, a small amount, generally 1% by weight, of silicone fluid may be added to all insecticidal/larvicidal embodiments of the invention to lower surface tension in the presence of moisture and thereby aid in spreading. The chemical description of a preferred silicone fluid, specified because of its approved use in foods eaten by humans under 21 CFR §176.200, is:

Dimethylpolysiloxane Silicone fluid CAS No. 63148-62-9* Nominal Viscosity, 77° F.: 350 ctks (Only viscosity FDA-approved for food use)

The silicone fluid (dimethylpolysiloxane) varies in viscosity from 10 to 350 centistokes, and is added to the insecticide, repellent and/or larvicide at a concentration of from 0.1 to 10% by weight of the insecticide, repellent and/or larvicide.

In some embodiments of the invention, it is preferable to mix the formulations with water to facilitate spraying larger areas infested with target pests. As is common with such oil-based ingredients, emulsions are formed with water aided by various surfactants, soaps and detergents. Some of these are toxic and hazardous to the environment, particularly those commonly found in best selling oil-based larvicides and insecticides. It is preferred that when two emulsifiers are used, one is hydrophilic and the other is lipophilic. Together in selected proportions and concentrations, they bond water and oils and facilitate the making of emulsions varying in stability as required by the end result. The two food-grade surfactants preferably used in the invention are identified below by their trade names, their generic names and by their USF&DA clearance numbers:

TWEEN 80, Polysorbate 80 POE 20 sorbitan monooleate 21 CFR §172,840

SPAN 80 Sorbitan monooleate 21 CFR 517 173.75

The following examples, in the opinion of the inventor, typically represent preferred embodiments of the invention.

EXAMPLE 1

A water-white clear insecticidal solution is prepared by mixing the following components together by weight percentage of the total weight in any order at room temperature:

| | |
|---|---|
| gamma-nonalactone | 0.024% |
| gamma-undecalactone | 0.049% |
| d-limonene | 4.015% |
| Silicone fluid | 1.000% |
| Fast evaporating white mineral oil | 94.912% |

After stirring for a few moments, the solution is stable and ready for use as a contact insecticide on flying and crawling insects, such as flies, cockroaches, ants, mosquitos, and others. It is best applied as a spray from a hand-pumped sprayer in a rather concentrated stream that thoroughly wets the target insect(s). In the case of crawling insects, the spray should thoroughly wet the insects, the path on which they crawl, and either side up of the path, to a foot or so away. The spray quickly kills wetted insects and will tend to keep ants from returning to a sprayed path for considerable periods of time thereafter. Sometimes a second spray a few hours later substantially increases efficacy.

EXAMPLE 2

A water-white clear repellent solution is prepared by mixing the following components together by weight percentage of the total weight in any order at room temperature.

| | |
|---|---|
| gamma-nonalactone | 0.024% |
| gamma-undecalactone | 0.049% |
| d-limonene | 4.015% |
| Anethole | 0.147% |
| Benzaldehyde | 0.245% |
| Benzoic Acid | 0.147% |
| Cinnamyl Alcohol | 0.098% |
| Oil of Pennyroyal | 0.098% |
| Musk Ambrette | 0.024% |
| Vanillin | 0.024% |
| Slow evaporating white mineral oil | 95.100% |

After stirring for a few moments, the solution is stable and ready for application to human skin and animal fur as an insect repellent against such insects as mosquitos, gnats, "no-see-ums", flies and others. It can be applied as a fluid from its container, as a spray from a hand-pumped sprayer, from a roll-on dispenser, and from an impregnated paper or cloth wipe in which the formulation is incorporated. The solution is comparatively slow drying and leaves the skin or fur moist for several hours during which time it is most effective in repelling insects. The components also act as a pleasant skin moisturizer. After the solution evaporates, it may be reapplied for continued protection.

EXAMPLE 3

A water-white clear solution can be prepared to act both as a larvicide against mosquitos breeding in water, and as an insecticide against flying and crawling insects attacking ornamental plants and growing food crops. Typical weight percentages per total weight are:

| | |
|---|---|
| gamma-nonalactone | 0.024% |
| gamma-undecalactone | 0.049% |
| d-limonene | 4.015% |
| Tween-80 (surfactant) | 1.000% |
| Span-80 (surfactant) | 0.850% |
| Fast evaporating white mineral oil | 70.434% |
| Slow evaporating white mineral oil | 23.478% |

After stirring for a few moments, the solution is stable and ready for use as a 100% GRAS oil-based larvicide or insecticide. For either application, it is convenient sometimes to make a fast-breaking oil-in-water emulsion for transport as a spray to large water or plant surfaces whereupon the oils remain to perform their functions, and the carrier water separates out. The amount of water carrier may vary, but in typical uses, up to 10 gallons of water may be used to transport one gallon of EXAMPLE 3 solution to the target area.

To properly use such an emulsion spray, the sprayer must have provisions to mix the water and oil phases continuously during operation. With the selected amounts of surfactants used in the above ingredient listing, a well-mixed oil-in-water emulsion spray will separate in a few seconds after striking the target with the oils adhering to perform their designated functions and the carrier water both evaporating and running off the target. Of the two oils, the fast drying component will kill adult insects and their larva and eggs, on contact, while the slower evaporating white mineral oil and the various fragrances will remain to coat the plant surfaces and repel other insects from landing on the crops.

Used as a mosquito larvicide, the solution as shown, with or without the carrier water, is applied to the surface of stagnant water in ponds, swamps and ditches in which mosquito larva breed. The EXAMPLE 3 formulation quickly spreads a microscopically thin film across the treated water surface, which acts to block larva from coming to the water-air interface to breathe. The amount of formula used depends upon the area to be treated as well as field conditions, the size of the mosquito population, and the weather.

Typically, from one to 15 gallons of the EXAMPLE 3 oils may be used per acre of treated surface, plus transport water as desired. Provisions must be made in the sprayer to mix the components during application. Larva are killed a few minutes after the formula is applied, while new growth is delayed for up to two weeks thereafter. Applications of EXAMPLE 3 several times monthly during the breeding season may be indicated.

EXAMPLE 3 is also effective for spraying row crops, fruit trees and vines to kill and repel insects. For optimum results, all upper and lower leaf and fruit surfaces should be completely wetted. Typical application rates can range from one to 10 gallons of the solution of EXAMPLE 3 per acre, depending on the target pest, density of the growing crop, temperature and other factors. Frequency of successive treatments during a growing season may vary from weekly to monthly. Mixed with water for transport to the target as a spray, the quick-breaking emulsion leaves plant surfaces covered with oils, while the water runs off to irrigate the vegetation.

While the invention has been described with reference to specific embodiments, examples, products and ranges, it will be obvious to those skilled in the art that modification may be made without departing from the invention which is specifically pointed out in the following claims.

What is claimed is:

1. A process for killing insects having a protective wax waterproofing coating covering their bodies to prevent desiccation comprising: wetting the insect with an effective amount of a solution of a generally regarded as safe (GRAS) composition consisting of 0.1 to 50% by weight, based on the total weight of said solution, of a GRAS terpene of the formula $C_{10}H_{16}$, optionally, 0.010 to 5.0% by weight, based on the total weight of said solution, of at least one GRAS aldehyde selected from the group consisting of gamma-undecalactone and gamma-nonalactone, optionally, 0.1 to 10% by weight, based on the total weight of said solution, of a GRAS silicone fluid, optionally, 0.1 to 5% by weight, based on the total weight of said solution, of at least one GRAS surfactant, and a GRAS fast evaporating white mineral oil to destroy the wax waterproofing coating by applying said solution as a spray engulfing said insect, said fast evaporating white mineral oil having a distillation initial boiling point of between 350° F. and 410° F., an end point of from 405° F. to 516° F. and a flash point of about 142° F. to 165° F.

2. The process according to claim 1, wherein said silicone fluid is a dimethylpolysiloxane having a viscosity of from 10 to 350 centistokes.

3. The process according to claim 1, wherein said surfactant is sorbitan monooleate, polyethoxylated sorbitan monooleate or a mixture thereof.

4. The process according to claim 1, wherein said terpene is d-limonene.

* * * * *